United States Patent [19]

Wagner

[11] 4,286,156
[45] Aug. 25, 1981

[54] DEVICE FOR DETERMINING THE SPATIAL ABSORPTION DISTRIBUTION IN A PLANE OF EXAMINATION

[75] Inventor: Wolfgang Wagner, Hamburg, Fed. Rep. of Germany

[73] Assignee: U.S. Philips Corporation, New York, N.Y.

[21] Appl. No.: 37,266

[22] Filed: May 9, 1979

[30] Foreign Application Priority Data

May 13, 1978 [DE] Fed. Rep. of Germany ....... 2821083

[51] Int. Cl.³ .......................... G01T 1/20; G21F 5/04
[52] U.S. Cl. ................................. 250/363 S; 250/511
[58] Field of Search ................. 250/360, 363 S, 445 T, 250/505, 511

[56] References Cited

U.S. PATENT DOCUMENTS

| | | | |
|---|---|---|---|
| 3,585,387 | 6/1971 | Bramlet | 250/505 |
| 3,840,747 | 10/1974 | Macovski | 250/363 S |
| 4,052,618 | 10/1977 | Hounsfield | 250/360 |
| 4,057,725 | 11/1977 | Wagner | 250/360 |
| 4,081,681 | 3/1978 | Froggatt | 250/360 |
| 4,143,273 | 3/1979 | Richey et al. | 250/445 T |

Primary Examiner—Alfred E. Smith
Assistant Examiner—Janice A. Howell
Attorney, Agent, or Firm—Thomas A. Briody; Robert T. Mayer; Jack E. Haken

[57] ABSTRACT

The device in accordance with the invention comprises detectors, a first part of which is not struck by radiation during measurement of the useful signal, whilst a second part which is struck directly by the radiation during the measurement of the useful radiation, is shielded during a next measurement. During the last measurement, the first detector part is struck by scattered radiation. From the two signals thus formed, a signal free from scattered radiation can be obtained by subtraction.

4 Claims, 5 Drawing Figures

DEVICE FOR DETERMINING THE SPATIAL ABSORPTION DISTRIBUTION IN A PLANE OF EXAMINATION

The invention relates to a device for determining the spatial absorption distribution in an object, comprising a plurality of radiation sources which are arranged in a plane of examination and which irradiate the plane of examination from different directions, and also comprising a large plurality of detectors which are arranged on an arc of a circle in the plane of examination and which serve to measure the intensity of the radiation on the other side of the object, at least a part of said detectors being struck by radiation from different directions. A device of this kind is known from U.S. Pat. No. 4,057,725. The device described therein enables very quick measurement of the absorption values required for determining the absorption distribution. When a sufficient number of radiation sources are available, mechanical movements are no longer required in such a device for measuring a slice, the individual radiation sources being consecutively flashed.

In devices of this kind, a detector is successively exposed to radiation from different radiation sources, (i.e. radiation from different directions in the plane of examination is incident on the detector). Thus no use is made of collimators for shielding against scattered radiation which are focused onto a radiation source and which are arranged in front of the detectors, so that the scattered radiation is particularly disturbing. The invention has for its object to provide a device of the kind set forth in which faults caused by the scattered radiation during the reconstruction of the absorption distribution are reduced.

This object is achieved in that a device in accordance with the invention is characterized in that in order to produce a first signal, detectors comprise a first zone which is shielded against radiation which passes along straight lines between source and detector and, in order to supply a second signal, comprise an adjoining second zone in a direction transversely of the plane of examination in order to detect radiation passing along straight lines between source and detector, both signals being usable for the formation of a difference signal.

The invention is based on the recognition of the fact that the output signal of the second detector zone which is directly exposed to the radiation of a radiation source comprises a useful component which is dependent of the absorption of the radiation in the plane of examination, and also a disturbing component which is superposed thereon and which is caused by the scattered radiation. The output signal of the first detector zone on which the useful radiation cannot be incident is proportional to the disturbing component, because the first detector zone is exposed to substantially the same intensity of scattered radiation as the second detector zone. The spatial distribution of the scattered radiation fluctuates only slightly in the relevant direction. The disturbing component generated by the scattered radiation can be eliminated from the output signal of the second detector zone by subtraction, taking into account a ratio factor, if any.

The two signals can in principle be obtained by a separate measurement. However, in that case the first and the second detector zone must be independent of each other, (i.e. each time at least two separate detector elements have to be used). This makes the device expensive. According to a further aspect of the invention, the number of detectors need not be increased if each detector comprises only one output and if an aperture is provided which is slidable perpendicularly to the plane of examination, said aperture releasing the second detector zone in a first position and shielding this zone in a second position, the output signal of each detector during a first measurement, when the aperture occupies one of the two positions, being stored in order to form the difference with respect to the output signal obtained during a second measurement during which the aperture occupies the other position. Preferably, the two detector zones have the same diameter in each plane which is parallel with respect to the plane of examination. During a first measurement, the second zone of the detector (i.e. that area which serves to form a signal which contains as well useful radiation as scattered radiation) is irradiated, while during the second measurement the first area which serves to supply a signal containing only scattered radiation is irradiated. The latter signal is substantially independent of local variations in the absorption, for example, caused by movements of organs, so that it is sufficient for the body to come to a rest between the two measurements. The intensity of the primary radiation may be substantially lower during the second measurement, when only the scattered radiation is measured, than during the first measurement, because the part of the scattered radiation does not contain higher components of the local frequency; as a result, the radiation dose for the patient is only slightly increased by the second measurement.

An embodiment of the device in accordance with the invention will be described hereinafter with reference to the drawing.

Figure 5:
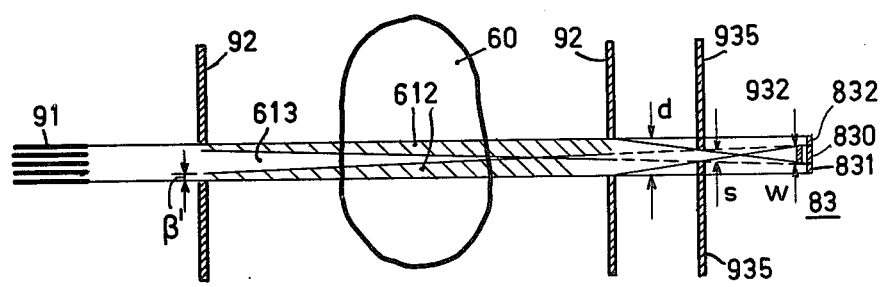
Figure 4:
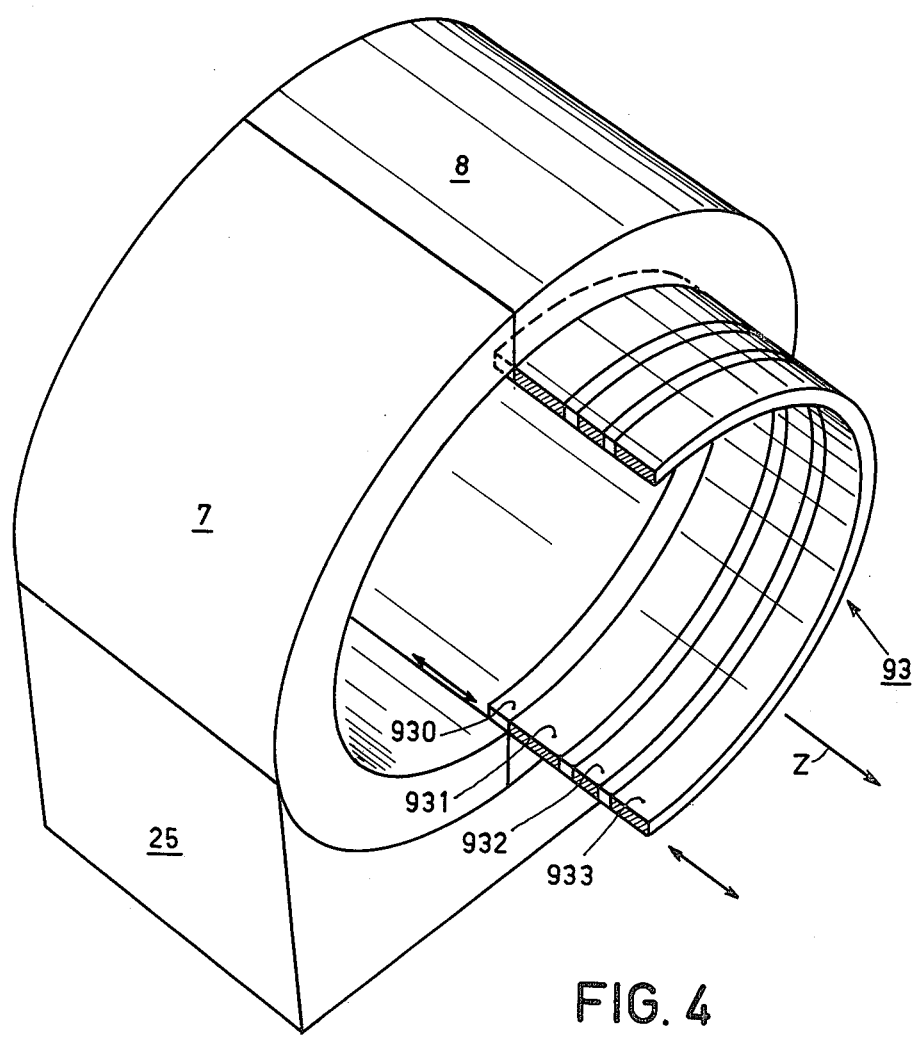

FIG. 4 diagrammatically shows a modified embodiment of the device in accordance with the invention; and FIG. 5 shows a further embodiment.

Figure 1:
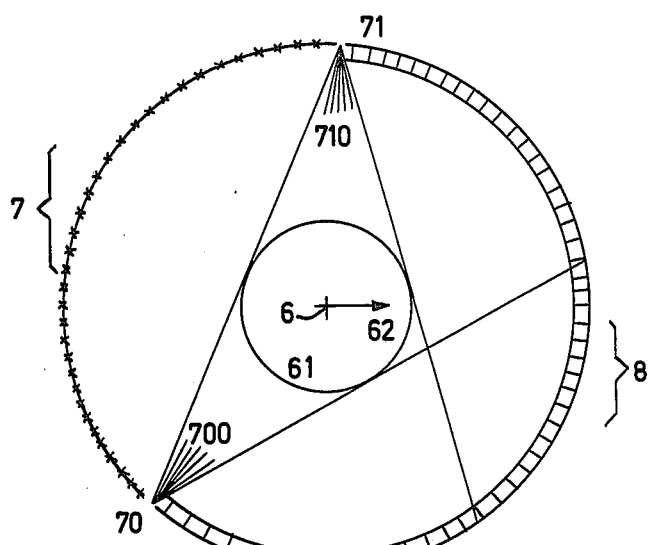
FIG. 1 shows the geometrical arrangement of the radiation sources and the detectors.

In the device which is diagrammatically shown in FIG. 1, the radiation sources and the detectors are arranged on a common arc of a circle, a part of the arc of a circle which is occupied by radiation sources, preferably X-ray tubes, being denoted by the reference numeral 7, while a part which is occupied by the detectors is denoted by the reference numeral 8. Extreme radiation sources 70 and 71 emit radiation beams 700 and 710 which completely irradiate an examination zone 61 which is concentric to the circular ring 7, 8 or the center 6 thereof, a patient to be examined being arranged within said examination zone. The device described thus far is known.

Figure 2:
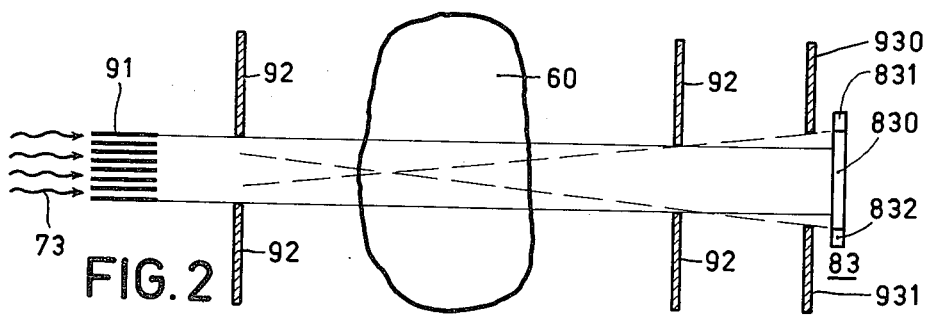

FIG. 2 is a sectional view taken along an axis 62, only one detector of the ring 7, 8 being shown. The radiation beam 73 emitted by a radiation source (not shown) passes through an aperture 91 which consists of several radiation-absorbing flat plates which are arranged at the same distance from each other and which are thin with respect to this distance. As a result, the emitted radiation passes through the plane of examination mainly parallel to the plane of examination or at a comparatively small angle with respect thereto. The radiation passing through the aperture 91 furthermore passes through a rigidly arranged, hollow cylindrical aperture device 92 which is concentric to the ring 7, 8 (FIG. 1) and which comprises an annular aperture having a width d, which corresponds exactly to the distance between the upper and the lower aperture plate of the aperture 91. The radiation passes through the body 60 of a patient situated within the circular cylindrical aperture device 92 and reaches, via the opposite ly situated part of the device 92, one of the detectors 83 arranged on the circular ring. The detector comprises a zone 830 which is directly exposed to the X-radiation or gamma radiation passing through the plane of examination without being scattered. Above as well as below this zone, the detector comprises a further zone 831 and 832, respectively, which cannot be struck by the radiation which passes through the plane of examination without scattering and which is shielded against scattered radiation from the plane of examination by parts 930 and 931 of an aperture device 93 which is displaceable perpendicularly to the plane of examination and which is only partly shown in FIG. 2. The detector 83 thus concerns an individual detector element whose measuring surface, for example, a face of a scintillation crystal, covers the zones 830, 831 and 832 and which generates, for example, via a photomultiplier, an (electric) output signal which is dependent of the zone of the measuring face which is struck by radiation as well as of the intensity of the radiation. This aperture device is shaped as an arc of a circle and is arranged to be concentric to the aperture device 92 or the circular ring 7, 8 (FIG. 1). However, it extends only in front of the part of the circular ring which is occupied by the detectors.

The aperture 91 is constructed so that radiation which passes between the upper plate and the adjacent plate or between the lower plate and the adjacent plate can also reach the zone 830. The drawing shows that the detector zone 830 has a length in a direction perpendicularly to the plane of examination which exceeds the value corresponding to the thickness d of the radiation beam. This length is not only dependent of the thickness d, but also of the diameter of the aperture device 92 and of the diameter of the circular ring on which the radiation sources and the detectors are arranged. For the sake of clarity, the thickness d of the irradiated layer (approximately 1 cm in practice) is strongly exaggerated in FIG. 2 with respect to the diameter of the plane of examination which is governed by the aperture device 92.

Figure 3:
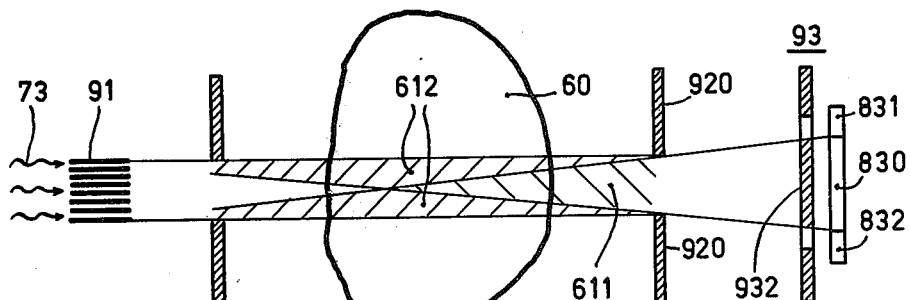
FIGS. 2 and 3 show the radiation path for the measurement of useful radiation and the scattered radiation, respectively.

FIG. 3 shows the same device as FIG. 2, be it that the aperture system 93 is shifted in a direction perpendicularly to the plane of examination, so that the part 932 thereof keeps the total direct radiation (i.e. non-scattered radiation) remote from the detector 83, notably from the zone 830 thereof. In practice, however, the proportions differ slightly from the proportions shown, because the actually three-dimensional geometry is replaced by a two-dimensional arrangement in order to simplify the description. However, the zones 831 and 832 which are situated above and below the zone 830 and which cannot be struck by the direct radiation in any position of the aperture system 93, are struck by scattered radiation produced in the plane of examination in this position. The scattered radiation influences the output signal of a detector 83 in different ways in any case: the scattered radiation produced in the shaded area 611 reaches the detector zone 830 as well as the detector zone 832, while the scattered radiation produced in both areas 612 can be incident on only one of the two zones.

As has already been stated, the intensity of the radiation 73 may be substantially smaller in the position of the aperture system 93 shown in FIG. 3 than in the position shown in FIG. 2, because the scattered radiation mainly contains only smaller components of the spatial frequency. Assuming that the output signal of the detector 83 amounts to $I_1$ during the first measurement (in accordance with FIG. 2) and that the output signal of this detector amounts to $I_2$ during the second measurement (FIG. 3), the measuring value I wherefrom the effect of the scattered radiation has been removed is obtained from the equation $I = I_1 - CI_2$. Therein, C is a factor which takes into account the different detection probability of the scattered radiation by the zone 830 during the first measurement (FIG. 2) on the one hand and the zones 831 and 832 during the second measurement (FIG. 3) on the other hand, and also the different radiation intensities during the two measurements. The factor C can be determined by a series of test measurements performed on phantom bodies whose geometry and absorption behaviour is known. The scattered radiation profile to be anticipated for the phantom body can each time be compared with the scattered radiation profile obtained in the two positions of the aperture system 93 and therefrom the factors C can be calculated after which they are stored.

During operation, therefore, the measuring value $I_1$ is temporarily stored after the first measurement; subsequently, the measuring value $I_2$ obtained during the second measurement is multiplied by the factor C and the product is subtracted from the value $I_1$.

For correcting the measuring value $I_1$ of a detector, however, it is not only possible to take into account the measuring value $I_2$ of the same detector obtained during the second measurement, but also the measuring values of the adjacent detectors obtained during this second measurement; the measuring values of the detector and of the adjacent detectors obtained during the second measurement are then subjected to a convolution operation which smoothes the scattered radiation spectrum, thus reducing the effect of quantum noise of the measuring values obtained during the second measurement.

FIG. 4 shows, shifted in a direction perpendicular to the plane of examination, the aperture system 93 in a computer tomography apparatus, the base 25 of which supports the circular ring with the radiation sources 7 and the detectors 8. Each time between two radiation-impermeable zones 930 and 931, 931 and 932, and 932 and 933, respectively, there are zones consisting of radiation-permeable material (for example, epoxy resin), so that the useful or scattered radiation, respectively, shown in the FIGS. 2 and 3, can pass through the aperture 93. The aperture system 93 is journalled to be displaceable on rails (not shown) in a direction perpendicular to the plane of examination (i.e. in the direction of the arrow Z) and is displaced by a stepmotor (not shown). The aperture system 93, extending over an arc of, for example, 200° C. (see FIG. 1), can be supplemented to form a complete, hollow cylinder by means of a part consisting of radiation-permeable material. The apertures 92 and 91 (FIG. 3) are not shown for the sake of clarity.

As appears from FIG. 5, illustrating a further embodiment for determining the scattered radiation, it is not absolutely necessary for the length of the detectors to exceed the thickness of the layer to be examined. In this case the aperture system 93 should in any case consist of two parts (932 and 935) which are situated at different distances from the center of the plane of examination. The area 932 which is situated closely in front of the detector 380 and whose length in the longitudinal direction corresponds to approximately half the thickness d of the radiation beam, shields a central zone 830 against direct X-radiation (useful or scattered radiation). The aperture portion 935 is situated at a large distance from the detector 83 and consists of two radiation-impermeable parts which leave an aperture s in the center, said aperture being proportioned so that the detector zones 831 and 832 which are not shielded by the aperture portion 932 cannot be struck by the direct X-radiation but are exposed to scattered radiation. As is shown in the drawing, radiation produced within the shaded area 612 in the plane of examination is detected by only one of the zones 831 and 832, while scattered radiation produced in the comparatively large intermediate area 613 cannot at all be detected by the detector zones 831 and 832. Thus, in total in this embodiment a low detection probability for the scattered radiation and a larger dependency of the detection probability on the location of appearance of scattered radiation than in the preferred embodiment according to the FIGS. 2-4 is obtained.

The invention can also be used in devices other than the configuration shown in FIG. 1. For example, the detectors and the radiation sources can be arranged on two complete, concentric circular rings, for example, as described in German Patent Application P 28 17 912. To this end, the parts 930, 931 and 933 of the aperture system 93 must be constructed to cover fully 360° C., while the part 932 may be limited to one half circle (like in FIG. 4). Moreover, the aperture system 93 must be provided with a second, stepmotor (not shown) which rotates the system around an axis which extends perpendicularly with respect to the plane of examination and through the centre 6 of the plane of examination. For generating the first detector signals, the aperture system 93 is then rotated and the sources situated opposite the part 932 of the aperture system 93 are successively flashed. Even though the time required for fully generating all first detector signals amounts to approximately 1 second, this duration is not an important drawback, because the motions of organs have very little effect on the spatial distribution of the scattered radiation intensity during this period as long as the body in total is in rest.

What is claimed is:

1. In a device for determining a spatial absorption distribution in an object, comprising a plurality of radiation sources which are arranged in a plane of examination and which irradiate the plane of examination from different directions, and also comprising a large plurality of detectors which are arranged on an arc of a circle in the plane of examination and which serve to measure the intensity of radiation which passes through the object, at least some of said detectors being struck by radiation from more than one direction, the improvement wherein:

the detectors comprise a first zone (831, 832) which is active to produce a first signal; and an adjoining second zone (830) which is disposed in the plane of examination and detects radiation which passes along straight lines between at least one source and the detectors in said second zone, and is active to produce a second signal; and the device further comprises shielding means which function to shield the first zone from radiation which passes along straight lines between the sources and the detectors in said first zone.

2. A device as claimed in claim 1, wherein each detector has only one output, and the shielding means comprise an aperture (93) which is slidable, perpendicular to the plane of examination, to expose the second detector zone to radiation (830) in a first position and to shield the second zone in a second position, and further comprising means which store the output signal of each detector when the aperture is in the first position then subtract the output signals, which are produced when the aperture is in the second position, from the stored signals.

3. A device as claimed in claim 1 or 2, in which the radiation sources are arranged on a first side (7) of an arc of a circle, the detectors are arranged on an other side (8) of the same arc of a circle, and the aperture system (93) comprises a hollow cylindrical portion (93) which is arranged within the arc (7, 8) and which covers the arc of a circle of the detectors.

4. A device as claimed in claim 3, further comprising a hollow cylinder (93) rigidly disposed concentric to the detectors and the radiation source, said cylinder including two concentric radiation-impermeable portions which are disposed above and below the plane of examination, and a radiation-permeable portion disposed between said radiation-impermeable portions.

* * * * *